US006284285B1

(12) United States Patent
Weis-Fogh (10) Patent No.: US 6,284,285 B1
(45) Date of Patent: Sep. 4, 2001

(54) TISSUE REPAIR PROMOTING COMPOSITION

(75) Inventor: Ulla Sivertsen Weis-Fogh, Hørsholm (DK)

(73) Assignee: E. R. Squibb & Sons, Inc., Skillman, NJ (US)

( * ) Notice: Subject to any disclaimer, the term of this patent is extended or adjusted under 35 U.S.C. 154(b) by 0 days.

(21) Appl. No.: 07/998,128

(22) Filed: Dec. 29, 1992

Related U.S. Application Data (63) Continuation of application No. 07/704,911, filed on May 21, 1991, now abandoned, which is a continuation of application No. 07/465,530, filed on Jan. 17, 1990, now abandoned, which is a continuation of application No. 07/216,712, filed on Jul. 5, 1988, now abandoned.

(30) Foreign Application Priority Data

Oct. 3, 1986 (DK) ................................................ 4753/86
Oct. 2, 1987 (WO) ................................ PCT/DK87/00117

(51) Int. Cl.[7] ................................................ A61K 35/16
(52) U.S. Cl. .......................... 424/529; 424/530; 424/531; 424/532; 424/534; 514/2; 514/21; 530/380; 530/381; 530/383
(58) Field of Search ..................................... 424/529, 530, 424/531, 532, 534; 514/2, 21; 530/380, 381, 383

(56) References Cited

U.S. PATENT DOCUMENTS

| | | | |
|---|---|---|---|
| 2,710,294 | 6/1955 | Garlough et al. | 530/364 |
| 3,223,083 | 12/1965 | Cobey | 606/92 |
| 3,870,042 | 3/1975 | Viguier | 604/406 |
| 3,986,506 | 10/1976 | Garber et al. | 604/406 |
| 4,278,594 | 7/1981 | Amrani | 530/383 |
| 4,298,598 | 11/1981 | Schwarz et al. | 424/94.64 |
| 4,341,764 | 7/1982 | Wallace et al. | 514/2 |
| 4,377,572 | 3/1983 | Schwarz et al. | 514/2 |
| 4,414,976 | 11/1983 | Schwarz et al. | 606/214 |
| 4,427,650 | 1/1984 | Stroetmann | 424/46 |
| 4,427,651 | 1/1984 | Stroetmann | 424/46 |
| 4,442,655 | 4/1984 | Stroetmann | 53/428 |
| 4,453,939 | 6/1984 | Zimmerman et al. | |
| 4,608,178 | 8/1986 | Johansson et al. | 210/744 |
| 4,608,254 | 8/1986 | Philapitsch et al. | 424/530 |
| 4,650,678 | 3/1987 | Fuhge et al. | |
| 4,714,457 | 12/1987 | Alterbaum | 494/37 |
| 4,735,616 | 4/1988 | Eibl et al. | |
| 4,740,498 | 4/1988 | Hirao et al. | |
| 4,760,131 | 7/1988 | Sundsmo et al. | 530/356 |
| 4,816,251 | 3/1989 | Seelich | |
| 5,165,938 | 11/1992 | Knighton | 424/532 |

FOREIGN PATENT DOCUMENTS

| | | |
|---|---|---|
| 514223 | 12/1978 | (AU) . |
| 552883 | 5/1983 | (AU) . |
| 035202 | 9/1981 | (EP) . |
| 253198 | 1/1988 | (EP) . |
| 261599 | 3/1988 | (EP) . |
| 2146335 | 4/1985 | (GB) . |
| 61-85304 | 4/1986 | (JP) . |
| WO 86/01814 | 3/1986 | (WO) . |

OTHER PUBLICATIONS

Farbiszewski et al., Biochim Biophys. Acta 115: 397–403 (1966).*
Senior et al., J Cell Biol. 96: 382–385 (1983).*
Epstein et al., *Ann. Otol. Rhinol. Laryngol.*, 95, 40–45 (1986).
Gestring and Lerner, *Vascular Surgery*, 294–304 (Sep./Oct. 1983).
Moretz et al., *Head And Neck Surgery*, 95, 122–124 (Jul. 1986).
Pearl et al., *Surgery, Gynecology & Obstetrics*, 144, 227–31 (Feb. 1977).
Siedentop et al., *Larynogoscope*, 95, 1074–1076 (Sep. 1985).
Wolf, *Arch. Otorhinolaryngol.*, 237, 279–83 (1983).

* cited by examiner

Primary Examiner—Jean C. Witz
(74) Attorney, Agent, or Firm—Jasper W. Dockrey; Brinks Hofer Gilson & Lione (57) ABSTRACT

A method for isolating tissue repair promoting substances from human or animal blood, which method comprises collecting the human or animal blood from a single human or animal individual in a first container of a container system comprising at least first and second interconnected containers; centrifuging the container system containing said blood so as to separate the blood in various fractions including a plasma fraction; transferring at least part of the plasma fraction to said second container of the container system; subjecting the plasma fraction in said second container to a low temperature so as to obtain a precipitate comprising tissue repair promoting substances; concentrating said precipitate in said second container so as to obtain a first fraction comprising a major part of the non-precipitated material, and a second fraction comprising at least the major part of the precipitate and a minor part of the non-precipitated material; and separating said second fraction comprising the tissue repair promoting substances from said first fraction within the second container; and optionally heating said second fraction within one of the containers of the container system so as to dissolve the isolated precipitated tissue repair promoting substances.

Furthermore, fractions comprising tissue repair promoting substances derived from blood cells may be isolated within the container system, said fractions optionally being combined with the second fraction comprising tissue repair promoting substances derived from blood plasma.

At least part of the fractions obtained may be kept for application to a tissue of the human or animal individual from whom the blood was collected.

12 Claims, 1 Drawing Sheet

TISSUE REPAIR PROMOTING COMPOSITION

This is a continuation of application 07/704,911, filed May 21, 1991, now abandoned which was a continuation of application Ser. No. 07/465,530 filed Jan. 17, 1990, now abandoned, which was a continuation of application Ser. No. 07/216,712, filed Jul. 5, 1988, now abandoned.

FIELD OF THE INVENTION

The present invention provides a simple, rapid, and inexpensive method and apparatus for small-scale preparation of tissue repair promoting substances needed in medical and veterinary practice. The substances are isolated from biological material obtained from human or animal individuals. The compositions comprising the biologically active substances prepared according to the invention offer significant benefits to the subject treated therewith in that they, in addition to efficiently promoting tissue repair, have few or no harmful side effects.

BACKGROUND OF THE INVENTION

In recent years several naturally occurring biological substances, especially from mammals, have been isolated and their biological properties have been established. Parallel to this development, fields of application of these substances have been discovered, and the need of suitable methods for their isolation have therefore increased. Examples of such substances are substances recovered from human blood, and methods for large-scale production using blood pooled from several donors have been developed.

However, the drawbacks of these large-scale production methods are numerous. First, the obtainment of blood from donors (voluntary or paid) causes well-known problems, such as the problem of limited access to a sufficient amount of biological material due to limitations with respect to the number of donors and the amount of blood which can be collected from the individual donor. Secondly, the collection procedures, storage and distribution of the material obtained require time and considerable financial ressources. Thirdly, the large-scale production of the substances under sterile conditions necessitates advanced and expensive equipment, and the waste of material during these numerous and laborious isolation steps is substantial.

Furthermore, the quality of the substances in the product obtained is substantially decreased compared to the quality of the substances present in the original native biological material. Thus, the yield of biologically active well-functioning substances may be very low. Storage of biological material over prolonged periods is known to result in spontaneous degradation of the various substances. Procedures (i.e. heating) employed in order to prevent/reduce the risk of transmission of infectious microorganisms substantially increase the extent of the denaturation of the substances and thus the loss of biological activity. A method which completely inactivates any kind and any amount of microorganisms and at the same time preserves the biological activity of the substances in question has not yet been developed.

A product prepared from numerous donors is inhomogeneous, and every component in the product represents a potential immunogen, i.e. administering the product to a human or animal individual in need thereof may result in harmful immunological reactions in said individual. The severity of such allergic/immunological reactions ranges from minor inconveniences to fatal anaphylactic reactions or disabling immunological diseases.

A field in which the administration of biological substances has become important is the field of promoting tissue repair, e.g. wound healing. It is now known that several substances contribute to the obtainment of tissue repair. During the repair of a tissue injury, chain reactions which release several substances occur, and these substances contribute to the body's mechanisms of tissue repair including hemostasis. Essential to this complex defence mechanism of the body are substances naturally present in whole blood. Some of these substances are present in plasma under normal conditions and undergo modifications during the tissue repair process. Other substances are under normal conditions present in the blood cells and are released from these cells during the tissue repair process.

Coagulation factors are substances in the blood that are essential to the clotting process and hence, to the maintenance of the hemostasis needed in tissue repair. Blood coagulation is the sequential process by which the multiple coagulation factors of the blood interact, ultimately resulting in an insoluble fibrin network. Coagulation factor I is also called fibrinogen. Fibrinogen can be converted into fibrin which forms the essential part of the blood clot. Fibrin is converted to an insoluble supporting network of fibrous material. The conversion takes place by the action of an enzyme such as thrombin. Coagulation factor VIII, also known as the antihemophilic factor, participates in blood coagulation. Coagulation factor XIII is the fibrin stabilizing factor. It polymerizes fibrin monomers so that they become stable and insoluble, thus enabling the formation of a stable clot.

Also participating in the coagulation processes are the platelet derived factors, the so-called platelet factors 1–4, e.g. platelet factor 2, which accelerates the thrombin-fibrinogen reaction. The platelet-derived growth factor (PDGF) is known as a potent mitogen, which e.g. promotes the proliferation of fibroblast cells needed in tissue repair. Furthermore, epidermal growth factor (EGF) which promotes epithelial growth is present in the platelets.

Another important component present in plasma is the protein fibronectin, which plays a role in cell proliferation and in fibrin interaction.

Knowledge of the molecular basis for the sequence of the biochemical phenomena involved in tissue repair has promoted the need for development of suitable isolation procedures for the various biochemical substances involved in the repair. Compositions comprising the isolated tissue repair promoting substances have many applications in medical and veterinary practice, e.g. in wound repair and in oozing surfaces, as control of local bleeding, e.g. in liver and spleen repair, in prevention of peritoneal adhesion-formation by local fibrin sealing, as closure of postoperative fistulae, and as fixation of skin grafts. The application of a composition containing tissue repair promoting substances in a concentrated form to a mammal in need of the treatment, e.g. treatment of a surgical wound, may shorten the wound healing period considerably.

An important aspect of the use and manufacture of compositions comprising tissue repair promoting substances is the employment of the composition for achieving substantial intermediary initial adhesion between injured tissue surfaces. E.g. wound healing an be efficiently promoted by topically applying a composition comprising fibrinogen in a concentrated form to a mammal in need of the treatment, and at the same time providing means for the enzymatic conversion of the fibrinogen to a firm supporting fibrous network. The use of such a tissue-adhesive system will probably increase, especially in surgical practice where it provides excellent means for obtaining hemostasis, closing leakages from fluid containing compartments etc.

The isolation and use of fibrinogen compounds for tissue repair is well-known, cf. AT No. 359,653, DE No. 3,002,934, DE No. 3,203,775, DE No. 3,105,624, EP No. 0,068,047, WO 86/01814 and EP No. 0,068,149.

These known methods are typically large-scale preparations of substances from a blood pool obtained from more than one donor, often from a blood pooled from several hundreds or thousands of individual donors. Furthermore, the procedures usually involve several laborious purification steps such as repeated washing procedures. Usually lyophilization, which is a laborious time- and material-consuming procedure, is employed. Sterilization procedures such as sterile filtration are often needed. The overall recoveries of biologically active substances recovered by such procedures are low.

SUMMARY OF THE INVENTION

The object of the present invention is the provision of a simple and inexpensive method for small-scale production of substances useful in tissue repair, in particular substances isolated from blood plasma, e.g., coagulation factors, and substances derived from blood cells, such as the platelet-derived growth factor (PDGF).

The present invention provides a method for the production of a composition comprising tissue repair promoting substances such as the coagulation factors fibrinogen and factor XIII, and the adhesive protein fibronectin. Furthermore, the composition may comprise tissue repair promoting substances derived from blood cells such as leucocytes or platelets, e.g. the platelet-derived growth factor (PDGF) and epidermal growth factor (EGF).

The invention further provides an apparatus or system for the preparation of tissue repair promoting substances, said apparatus permitting the preparation to be performed rapidly and with minimum use of expensive advanced equipment. The apparatus is small (the overall weight of the apparatus typically being less than one kg), i.e. it can easily be transported to the donor of the biological material, sealed from the environment, and subsequently easily transported to a laboratory having conventional equipment such as a centrifuge and a cooling bath.

In its broadest aspect, the method of the invention comprises a) collecting the human or animal blood from a single human or animal individual in a first container of a container system comprising at least first and second interconnected containers, b) centrifuging the container system containing said blood so as to separate the blood in various fractions including a plasma fraction, c) transferring at least part of the plasma fraction to said second container of the container system, d) subjecting the plasma fraction in said second container to a low temperature so as to obtain a precipitate comprising tissue repair promoting substances, e) concentrating said precipitate in said second container so as to obtain a first fraction comprising a major part of the non-precipitated material, and a second fraction comprising at least the major part of the precipitate and a minor part of the non-precipitated material, and f) separating said second fraction comprising the tissue repair promoting substances from said first fraction within the second container, and g) optionally heating said second fraction within one of the containers of the container system so as to dissolve the isolated precipitated tissue repair promoting substances.

In a further aspect, the invention provides a method for preparing a fraction comprising tissue repair promoting substances for a single human or animal individual, said fraction being kept for application to a tissue of the human or animal individual from whom the blood was collected.

The method may, e.g., be performed as follows: Blood is collected from a single human or animal individual. The blood may be collected from a single healthy donor or from an individual in need of tissue repair. The blood collection may be performed several weeks or months prior to use, or, preferably within a short period prior to use.

The blood is collected directly into a collection system comprising at least two containers interconnected so as to enable transfer of material from one container to an other without establishing contact with the environment. Transfer of material between the containers of the system can be performed by external manipulation of the system, and separation and isolation may be performed by precipitation and centrifugation. A precipitation enhancing agent may be added to the system prior to the collection of the blood.

The method according to the invention permits the preparation of all substances within a closed sterilized system. Thus, the resulting fraction for the promotion of tissue repair can be used directly from one of the containers of the container system without being subjected to laborious washing or sterilization procedures. The fraction which comprises a large amount of fibrinogen is isolated within one of the containers and can be used directly as a component in e.g. a tissue-adhesive system. The fact that the yield of the fibrinogen component is very high provides for the possibility of preparing a large amount of tissue-adhesive material from only a small amount of blood.

Since the substances obtained are to be used in the treatment of a living human or animal individual, every step of the procedure must be performed so as to exclude the possibility of the material being contaminated from the environment. One aspect of the present invention is to provide an apparatus comprising interconnected closed containers, the apparatus permitting the preparation to be performed so that all substances are prepared within a closed system. Immediately after the collection of the biological material, the access to the inner of the apparatus is sealed and during all the processing steps, the system is closed, i.e. no direct access to the environment is established. This feature of the method and apparatus makes the application possible in a routine laboratory not having access to facilities usually employed during operations under sterile conditions. The collection of the biological material, e.g. the puncturing of a blood vessel, must be performed by a person skilled in obtaining biological material under sterile conditions. Thus, this first step of the procedure may be performed by e.g. a technician skilled in collecting blood samples from patients. Immediately after the collection, the collection conduit is sealed and during all the subsequent steps the system is sealed from the environment, and these steps may therefore be performed by a person not skilled in the sterile techniques.

The advantages of the present invention can be summarized as follows:

the method provides a very high yield of the biologically active substances;

the procedure can be performed rapidly, i.e. within approximately ½–2 hours;

the preparation of the substances may be performed shortly before use, thus problems concerning stability over longer storage periods are totally avoided;

the whole procedure is performed in such a way that contamination from the outside is avoided, i.e. the resulting product is obtained in a form immediately suitable for therapeutic application;

tissue repair promoting substances from blood cells can be prepared simultaneously with the preparation of tissue repair promoting substances from blood plasma, as explained in greater detail below;

the risk of transmission of microorganisms and immunogen from foreign donors is minimized.

the tissue repair promoting substances are not subjected to potentially activity reducing procedures such as heating sterilization and lyophilization.

the substances may be prepared at very low costs.

The isolated substances may be used in a tissue-adhesive system, said system comprising as the main component fibrinogen to be used as a precursor for fibrin which in turn will participate in the formation of a stable fibrin clot. The composition according to the invention may be applied simultaneously with a solution containing a fibrinogen-activating enzyme such as thrombin, for example applied by way of two syringes connected by tubings adapted so as to ensure that the two solutions are not mixed prior to application to the tissue to be repaired. Such an application method provides excellent means for avoiding inconvenient clogging of the application system during operation. A further advantage of this application method is that it enables application of the substances at a site distant from the syringes, i.e. application can be performed for instance to fistulae distant from the exterior surface of the body or to the wound caused by biopsying inner organs.

The method permits the simultaneous isolation of tissue repair promoting substances derived from blood cells such as platelets, thus conferring valuable properties to the product. It is well-known that certain factors such as the platelet-derived growth factors (PDGF) promote the proliferation of mesenchymal cells thus contributing to the process of tissue repair. When the tissue-adhesive system is applied to a tissue to which the blood perfusion is low and hence the amount of platelets is low, the application of platelet-derived factors may be an advantage. The method and apparatus according to the invention permits the simultaneous preparation within the same system of several tissue repair promoting substances, i.e. several substances naturally present in blood plasma and several substances naturally present in blood cells such as platelets.

An important advantage of the method according to the invention is that it is readily applicable in combination with ordinary blood bank routine. Thus, the method provides the means for preparing tissue repair promoting substances simultaneously with the preparation of the well-known blood fractions prepared from donor blood, i.e. at least a minor part of the donated blood material can be used for the preparation of tissue repair promoting substances whereas the remaining blood material can be used for the preparation of clinically important fractions such as the erythrocyte containing fraction, the buffy coat (platelets and leucocytes) fraction etc. The container comprising the prepared tissue repair promoting substances may be stored together with the containers comprising the other prepared blood fractions. This provides for the possibility of administering the blood fractions such as the erythrocyte fraction and the fraction comprising the tissue repair promoting substances obtained from one donor to one patient, e.g. a patient undergoing major surgery and thereby needing both a transfusion of erythrocytes and repair of a surgical wound. Thus, the risk of transmitting infectious diseases by administering the tissue repair substances to an individual in need thereof, is not augmented compared to the risk of transmitting infectious diseases via the erythrocyte transfusion which was administered in any case.

The above-mentioned blood bank aspect of the invention provides considerable practical and economical advantages:

the blood material is utilized in a way that ensures a minimum loss of the valuable blood material;

the routine procedures employed in the blood bank are not disturbed—on the contrary, the administrative resources being employed in checking and calling upon the donors, collecting, handling, storing and distributing the blood material are fully utilized. An important part of this is the utilization of the extensive (and expensive) machinery employed in the testing of the donors for diseases, first of all infectious diseases such as hepatitis and AIDS;

no extra specialized personnel or equipment is needed for the preparation, the fraction comprising the tissue repair promoting substances is automatically classified and marked according to the blood group of the donor, and this provides for the possibility of administering the composition comprising the tissue repair promoting substances in accordance with this classification.

A further important advantage of the invention is that it permits the isolation of biological substances in such a way that the donor of the starting material for said substances is identical to the recipient of said isolated substances. Thus, the method makes it possible to isolate blood substances from blood collected from only one donor and further applying the resulting product to a tissue of said donor. By this procedure the risk of transferring foreign microorganisms from sick donors to the recipient, e.g. the risk of transmitting AIDS or hepatitis virus is totally avoided, and what is also of importance, the transferred amount of foreign immunogens is minimized.

In another important aspect, the present invention relates to an apparatus for carrying out the method of the invention, comprising first and second containers of a type defining a reducible inner volume, a blood inlet conduit connected to the first container and including a first closure valve, a conduit interconnecting the first and second containers and including a second closure valve, and optionally a further container or several further containers connected thereto and, when several further containers are present, interconnected, by means of a conduit (conduits) including a closure valve (closure valves).

More specifically, at least one of the containers may be a syringe cylinder comprising a piston member displaceably arranged or a collapsible flexible bag. Such a bag may be supplied with means permitting the subdivision of the bag into two or more individual chambers, in particular pinching means.

DETAILED DESCRIPTION OF THE INVENTION

The collection of blood may be performed within a few hours such as ½ or 1 hour, or the day before the use of the tissue repair promoting substances. Alternatively, the preparation may be performed several weeks before use of the preparation.

The blood is collected from a vein of the donor, preferably by puncturing the vein by means of a sterilized hollow needle, said needle being connected to a tubing which in turn is connected to the first container of the collecting system according to the invention. Alternatively, the blood may be collected from an outlet device mounted to the one end of a catheter placed in the vein of a donor—this alternative being applicable if sterile conditions are ensured during the collection.

The amount of collected material can be adapted to suit the particular purpose. Thus, if the blood is to be collected from e.g. a healthy voluntary donor the usual amount of collected blood is in the order of 400–600 ml, and at least part of said amount may be used for the preparation of tissue repair promoting substances.

If the blood is to be collected from a donor in need of treatment with the tissue repair promoting substances, the volume of the collected blood may appropriately constitute no more than a few % of the donor's total blood volume. If the subject to be treated is an adult human being, for instance 25–50 ml blood will be appropriate for the production of a preparation suited for most purposes.

The components of the container system is preferably made from material which optimally does not exude damaging substances to the biological material contained within the system. Furthermore, the material should be able to tolerate sterilization procedures usually employed for material which is to be used for clinical purposes. The sterilized system may, apart from the pathway used to collect the biological material, be constructed so as to exclude during operation direct contact between the internal spaces of the closed system and the environment.

Depending on the method selected for the fractionation of the blood obtained, the container system may comprise from two to six or more interconnected containers. Any agents needed during the preparation of the various fractions may be supplied to the containers of the container system prior to collecting the blood. The container system may then be sterilized after supplying the containers with the various agents so as to maintain the sterility of the spaces defined by the system.

The blood is collected into a first container of a container system comprising first and second interconnected containers, in some cases more interconnected containers. Since the first container of the container system is to be used for the blood collection, it should contain anticoagulants. Some of the conventional anticoagulants may be employed: citrate, acid-citrate dextrose (ACD), citrate-phosphate-dextrose (CPD), or ethylene diamine tetra-acetic acid (EDTA). Furthermore, heparin may be added in an amount sufficient for the prevention of thrombin activity during the processing steps. Proteolytic enzyme inhibitors, such as aprotinin $\epsilon$-aminocaproic acid or tranexamic acid may be added in order to prevent proteolytic degradation of the substances.

The container used for collecting blood may be a collapsible flexible bag, preferably a plastic bag. Alternatively the first container may be a syringe cylinder comprising a displaceably arranged piston member.

During collection of the blood into the first container, said container is preferably gently agitated to mix the blood with the chemical agents supplied to said first container of the system. After finishing the blood collection the tubing previously used for the blood collection is sealed. The sealing may be obtained by pinching the tubing with e.g. a clip. Alternatively, a closure valve may be positioned so as to block the contact between the inner space of the container system and the environment. The container system may e.g. comprise closure valves to be used in directing the liquid flow in the containers and tubings of the system. The tubing employed in the collection of the blood may at this stage be disconnected from the container system.

The container system is subsequently centrifuged in a conventional way so as to separate the blood in various fractions. The container system may be placed in a centrifuge holder without any of the interconnected containers being disconnected. This may be obtained by employing a specially adapted centrifuge holder. By adjusting the gravity forces employed, the blood may be separated into the following fractions:

a first fraction essentially comprising plasma and a second fraction essentially comprising blood cells including the major part of the erythrocytes, or a first fraction essentially comprising plasma and a minor fraction of some of the blood cells such as the platelets, and a second fraction comprising the major part of the blood cells including the major part of the erythrocytes, or a first fraction essentially comprising plasma, and a second fraction comprising essentially a part of the blood cells such as the platelets and leucocytes, and a third fraction comprising at least the major part of the erythrocytes.

After the centrifugation, parts of the fractions obtained by the centrifugation are transferred to the other containers of the container system and the tissue repair promoting substances are isolated within the containers.

The important step for isolating tissue repair promoting substances naturally present in the plasma of normal human or animal blood is a step comprising precipitation of said substances. These substances may be fibrinogen, factor VIII, factor XIII, and fibronectin. The precipitation may be obtained by subjecting the plasma-containing fraction to a low temperature, e.g. temperatures below 10° C., preferably below 4° C., more preferably in the interval from −80° C. to 2° C., especially in the interval from −30° C. to −10° C. Whenever frozen fractions are obtained, a step comprising thawing is employed, e.g. thawing the fractions at temperatures in the interval from −3° C. to 4° C.

The precipitation may be promoted by adding a precipitation promoting agent to the plasma fraction prior to or during subjection of the plasma fraction to a low temperature. The agent may be a lower alkanol such as a $C_{1-4}$-alkanol, e.g. methanol, ethanol or isopropanol, preferably ethanol, e.g. in a concentration of 1–30% w/w such as 3–20% w/w, preferably 6–11% w/w; or a lower alkyl ether such as diethyl ether in a concentration of 5–12% w/w, preferably 10–11%. Additionally, the agent may be an amino acid, e.g. lysine or glycine in a concentration of 0.1–3 M, preferably 2.2 M. The pH in the solution during the precipitation is preferably in the range of 5–9, preferably in the range of 6–8. The precipitation may also be promoted by changing the ionic strength of the solution by way of adding various salts such as ammonium sulphate or by adding polyethylene glycol or ethacridine. The precipitation promoting agents described above may be used alone or in combinations comprising two or more of the various agents. When suitable chemical agents are added, the precipitates may optionally be obtained without freezing the fractions, e.g. employing temperatures in the interval from −3° C. to 10° C., preferably from −3° C. to 4° C.

The tissue repair promoting substances naturally present in blood cells may be obtained from the cells by subjecting the cells to variations in temperature. A procedure involving freezing and subsequent thawing of the cells causes disruption of the cellular structures thereby releasing the comprised substances. Thus, growth factors may be released from platelets by subjecting the platelets to freezing and thawing procedures. Furthermore, specific agents added to the cell-containing plasma fractions may cause release of certain tissue repair promoting substances. The addition of substances such as adenosine diphospate, adrenalin, thrombin or collagen to platelets may cause the release of platelet-derived growth factors. Thus, the word "release" should, in the present description and the accompanying claims, be understood to apply to both specific cellular release and to the release of substances obtained by disruption of the cells, obtaining e.g. a cellular extract.

A way to concentrate the precipitate within the second container is to use natural gravity forces to sediment the precipitate within said second container, i.e. allowing the container to stand for a while in order to sediment the precipitate. Alternatively, the precipitate is concentrated in the second container by means of centrifugation whereby the precipitate is concentrated in the pellet obtained and thus separated from the non-precipitated material comprised in the supernatant.

The second fraction comprising the precipitated tissue repair promoting substances may be isolated within the second container by discharging the first fraction comprising the major part of the non-precipitated material. Said discharging may be carried out without establishing any contact to the environment by transferring the first fraction to a third container of the container system.

In another preferred method according to the invention, the second fraction is isolated from the first fraction within the second container by dividing the volume of the second container into first and second chambers containing said first and second fractions, respectively. The isolation of the second fraction within the second container may be carried out by employing a container comprising collapsible flexible wall parts as the second container of the container system and dividing the volume of said second container into first and second chambers by pinching said flexible wall parts.

The second or third container of the container system used in the method described above, may preferably be supplied with precipitation agents prior to use of said system.

Another preferred method according to the invention is to prepare a fraction comprising tissue repair promoting substances obtained from both the blood plasma and the blood cells. This is obtained by employing the following sequential steps:

a) centrifuging the container system containing the blood so as to separate the blood into various fractions including a cell-containing plasma fraction, b) transferring at least part of said cell-containing fraction to the second container of the container system, c) sedimenting the cells at the transferred fraction within the second container, d) making a primary temporary division of the volume of the second container, said division dividing the second container into a first chamber containing the sedimented cells and a minor part of the plasma and a second chamber containing the major part of the plasma, said division preferably being obtained by pinching the wall parts of the second container, e) subjecting the second container to a low temperature so as to obtain a precipitate in the second chamber, and so as to disrupt the cellular structures of the cells contained in the first chamber thereby releasing tissue repair promoting substances from the cells, thus obtaining a fraction enriched with tissue repair promoting substances released from the cells, f) sedimenting the precipitate within the second chamber, thus obtaining a second fraction within said second chamber, said second fraction comprising at least the major part of the precipitate and a minor part of the non-precipitated material, and at the same time sediment the major part of the cells and the cell residues within the first chamber, g) further subdividing said first chamber into a first "waste chamber" containing the sedimented cell residues and a third chamber containing a third fraction, said third fraction comprising at least the major part of the fraction enriched with tissue repair promoting substances released from the cells and being substantially free of cells and cell residues, h) further subdividing the second chamber into a second "waste chamber" containing the major part of the non-precipitated material and a fourth chamber containing at least the major part of the second fraction, and i) optionally, abolishing the primary temporary division of the second container, e.g. by removing the pinching of the wall parts, thus obtaining a combined chamber comprising the former third chamber and former fourth chamber. In doing so, the third fraction enriched with tissue repair promoting substances released from the cells was combined with the second fraction comprising the major part of the precipitate within the same container, j) and optionally heating the second fraction or the optionally combined fraction within the second chamber or within the optionally formed combined chamber so as to dissolve the precipitated tissue repair promoting substances.

In a preferred embodiment of the invention, the second container of the container system includes flexible wall parts, and the divisions of the volume of the second container are performed by pinching said flexible wall parts.

Thus, minimum loss of material during the procedures was ensured, this special feature of the method adding to the excellent high yield of biologically active substances.

In the method of the invention, precipitation promoting agents can be added to the plasma fraction contained in the second chamber prior to or during subjecting the second chamber to a low temperature. Said agents may be contained in a third container of the container system until the primary temporary division of the second container has been carried out.

Furthermore, specific agents suited for promoting the release of tissue repair promoting substances from blood cells may be added to the fractions comprising the cells. These agents may be supplied to a container of the container system prior to use. Said specific agents may be employed in combination with the obtainment of the cellular extracts by means of freezing/thawing procedures.

In a preferred method, a fraction comprising a major part of the blood plasma and a major part of the platelets is transferred to the second container, and subsequently tissue repair promoting substances derived from both the blood plasma and the platelets are isolated within the chambers of the second container, and optionally finally combined.

If, for some reason, the second and third fractions obtained in the chambers are needed separately, the combination step is omitted. Furthermore, the method and container system according to the invention may be used solely for preparing tissue repair promoting substances derived from blood cells, i.e. the plasma precipitation steps may be omitted, and the plasma may be used for alternative purposes or discarded.

Another preferred method comprises the following steps:
a) collecting the blood into a first container of a container system comprising at least first, second, third, and fourth containers,
b) centrifuging the container system containing said blood so as to separate the blood in various fractions including a substantially cell-free plasma fraction and a cell-containing plasma fraction,
c) transferring at least part of the substantially cell-free plasma fraction to the second container of the container system,
d) transferring at least part of the cell-containing plasma fraction tb the third container of the container system,
e) subjecting the substantially cell-free plasma fraction in the second container to a low temperature so as to obtain a precipitate comprising tissue repair promoting substances derived from plasma,
f) concentrating said precipitate within the second container so as to obtain a first fraction comprising a major part of the non-precipitated material and a second fraction comprising at least the major part of the precipitate and a minor part of the non-precipitated material, and separating said second fraction comprising the tissue repair promoting substances from the first fraction within the second container,
g) optionally discharging the first fraction to the fourth container,
h) subjecting the cell-containing fraction in the third container to a procedure which promotes the release of tissue repair promoting substances from the cells thus obtaining a fraction enriched with tissue repair promoting substances from the cells,
i) sedimenting the cells and cell residues within the third container thus obtaining a third fraction enriched with tissue repair promoting substances and substantially free of cells and cell residues,
j) separating said third fraction from at least the major part of the sedimented cells and cell residues within the third container and optionally transferring at least part of said third fraction to the second container, thus combining the third and second fraction, and
k) optionally heating the optionally combined fraction within the second container so as to dissolve the precipitated tissue repair promoting substances.

In a preferred embodiment of the invention, the third fraction is separated from at least the major part of the sedimented cells and cell residues by dividing the volume of the third container into first and second chambers containing said third fraction and the major part of the sedimented cells and cell residues, respectively. The third container may include flexible wall parts and the third container may be divided by pinching said flexible wall parts.

The sedimentation rate may be increased by means of centrifugation.

The procedure for promoting the release of tissue repair promoting substances may be a procedure involving freezing and thawing of the cells so as to disrupt the cellular structures of the cells and thereby releasing the tissue repair promoting substances. Furthermore, chemical agents suitable for promoting release of tissue repair promoting substances may be added to the cell-containing fraction.

The method may be carried out so that the cell-containing plasma fraction is a platelet-containing plasma fraction, e.g. comprising the major part of the platelets.

An important aspect of the method is that a sterilized container system may be employed, and the collection of the blood in the first container and the further steps identified are performed without establishing any direct contact between the fractions within the container system and the environment so as to obtain the fractions comprising the tissue repair promoting substances free from any contamination from the environment.

The precipitation promoting agents may be added to the plasma fraction prior to or during the subjection of the second container to a low temperature.

The tissue repair promoting substances which may be prepared from the plasma fraction are fibrinogen, factor VIII, factor XIII, and fibronectin.

The tissue repair promoting substances released from platelets may comprise platelet-derived growth factor and epidermal growth factor.

Optionally, these fractions may be used separately or a combined fraction may be isolated within one of the containers of the container system, said combined fraction comprising e.g. fibrinogen, factor VIII, factor XIII, fibronectin, and substances derived from platelets.

Furthermore, a tissue repair promoting composition comprising fibrinogen, factor VIII, factor XIII, fibronectin and substances derived from platelets, the composition being substantially free of fibrin, may be prepared according to the method of the invention.

The compositions according to the invention may be used for the promotion of tissue repair in a human or animal individual.

A further aspect of the invention is to provide a method for isolating tissue repair promoting substances including fibrinogen from human and animal blood, which method comprises
a) collecting a blood sample from the human or animal individual,
b) recovering more than 60% of the fibrinogen present in the blood sample in a form suited for application to a human or animal individual, the fibrinogen typically being concentrated approximately 10–20 times.

The fibrinogen concentration of the compositions prepared according to the methods of the invention usually is in the range of 20–45 mg/ml, often 25–35 mg/ml. Thus, the fibrinogen is concentrated approximately from 10 to approximately 20 times the concentration in plasma. Solutions with fibrinogen concentrations exceeding approximately 40 mg/ml may have a tendency to gelate at room temperature. However, this problem is easily solved, since resolution is achieved by incubating the solution at e.g. 37° C. for a few minutes.

The yield of fibrinogen is usually in the range of 60–95%, often more than 70%, usually approximately 70–85%, of the fibrinogen content in the starting material, the fibrinogen being quantified by means of a functional assay measuring the amount of biologically active fibrinogen.

The concentration of factor XIII in the solution prepared was usually in the order of 20–25 times the concentration of factor XII in the plasma fraction of the blood samples collected.

A further aspect of the invention is to provide a method for promoting the repair of a tissue of a human or animal individual, which method comprises
 a) collecting a blood sample from the human or animal individual,
 b) preparing tissue repair promoting substances from said blood sample, and
 c) applying said prepared tissue repair promoting substances to the tissue of said human or animal individual.

BRIEF DESCRIPTION OF THE DRAWINGS

The invention will now be further described with reference to the drawings, in which.

DETAILED DESCRIPTION OF THE DRAWINGS

Figure 1:
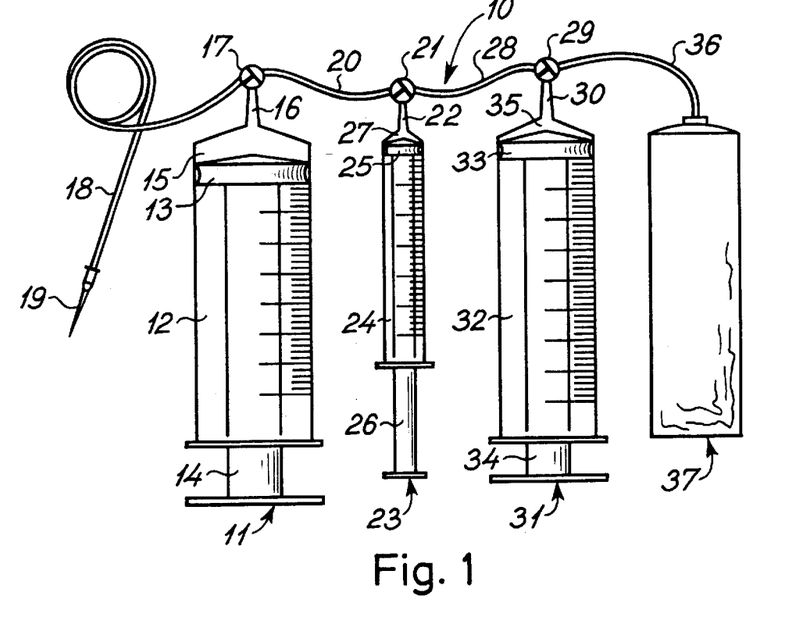
FIG. 1 is a diagrammatic side view of a first, presently preferred embodiment of an apparatus according to the invention.

In FIG. 1 a preferred embodiment of an apparatus or system according to the invention is shown designated 10 in its entirety. The isolating device 10 comprises two or more containers connected by means of tubings and valves for directing and stopping the flow of the liquids contained in the apparatus. The apparatus is preferably made from suitable materials such as plastics materials, which are preferably capable of withstanding sterilizing procedures or processes such as radiation treatment including UV radiation, or hydrogen peroxide treatment.

In FIG. 1 the system 10 comprises 4 containers which in their entirety are designated 11, 23, 31, and 37. The containers 11, 23, 31 are syringes, i.e. containers suitable for manipulating the content by means of operating a piston, whereas the container 37 is a bag of collapsible flexible plastics material. Alternatively two or one of the containers may be syringes comprising cylinders and pistons whereas two or three may be bags, such as collapsible flexible plastic bags. The bag or bags may be provided with outlet/inlet devices suitable for mounting sterilized tubings in a way which ensures that no contamination from the environment occurs. All the containers of the container system may be made of collapsible flexible plastic bags, preferred embodiments of the invention omprising four or five such bags. Furthermore, the container system may comprise five or more interconnected containers, some or all of the containers being bags, or some or all of the containers being syringes.

The pistons of the syringes may each be provided with screw coupling means to permit disconnection of the piston rod when the syringe is filled and is to be centrifugated. Alternatively, the syringes may be provided with piston rods being so short that when the piston rod is retracted to the desired position, the base of the piston flushes the base of the syringe cylinder so as to avoid further retraction during centrifugation. Devices for supporting the piston during centrifugation, especially when some of the syringe cylinders are empty or partly filled, may be employed. Thus, the piston rod may be used to manipulate the piston during emptying/filling of the syringe cylinder and further to support the piston during centrifugation. Another alternative is to employ a syringe comprising a piston provided with a string (instead of a piston rod) to be used in the manipulation of the piston.

In FIG. 1, the first syringe 11 comprises a syringe cylinder 12, a piston 13 and a piston rod 14, the piston 13 and piston rod 14 being provided with cooperating screw coupling means, bayonet coupling means or the like to permit disconnection of the piston rod 14 from the piston during centrifugation of the system. The piston 13 and the syringe cylinder 12 define a collecting chamber 15 suitable for storage of the collected biological material. The volume defined by the chamber 15 may, for example, be approximately 50 ml when the piston is maximally retracted from the delivery end 16, but it is, of course, also possible to have the volume smaller or larger, e.g. in the range from about 10 ml to about 200 ml or even 500 ml.

The delivery end 16 of the syringe 11 is connected to a three-way valve 17 which is connected to a tubing 18. The tubing 18 is provided with a hollow needle 19 suitable for puncturing a reservoir containing biological material, e.g., a blood vessel.

The three-way valve 17 is further connected to a tubing 20. The tubing 20 is connected to a three-way valve 21 which is connected to a delivery end 22 of a second syringe 23. The syringe 23 comprises a syringe cylinder 24, a piston 25 and a piston rod 26. The piston 25 and the cylinder syringe 24 define a chamber 27. The volume defined by the chamber 27 may, for example, be approximately 5 ml when the piston is maximally retracted from the delivery end 22 of the syringe 23, but analogously to what is stated above concerning the volume of the chamber 15, the volume of the chamber 27 may be smaller or larger, for example in the range from about ½ and 1 ml to about 20 ml or 50 ml, the volume of the chamber 27 normally being adapted to the volume of the remaining system, such as the volume of the chamber 15.

The three-way valve 21 is further connected to a tubing 28. The tubing 28 is connected to a three-way valve 29 which is further connected to a delivery end 30 of the syringe 31. The syringe 31 comprises a syringe cylinder 32, a piston 33 and a piston rod 34, which may be constructed in correspondence to the syringe cylinder 12, the piston 13, and the piston rod 14, respectively, of the first syringe 11. The piston 33 and the inner of the syringe cylinder 32 define a chamber 35. The volume defined by the chamber 35 may, for example, be approximately 30 ml when the piston is maximally retracted from the delivery end 30, but analogously to what is stated above, the volume may be smaller or larger, e.g. in the range from about 6 ml to about 120 ml or even 300 ml, the volume being adapted to the dimensions of the other containers of the system. The three-way valve 29 is further connected to a tubing 36 which is connected to a bag 37. The volume comprised by the bag may be approximately 40 ml but, as stated above, adapted to the dimensions of the other containers of the system.

Figure 2:
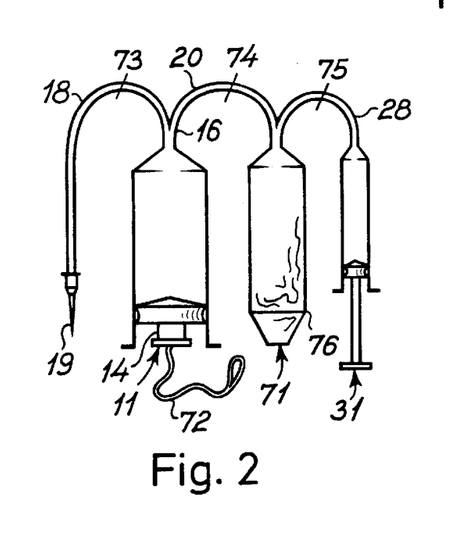
FIG. 2 is a diagrammatic side view of a second embodiment of an apparatus according to the invention.

In FIG. 2 a second embodiment of an apparatus or a system according to the invention is shown. The second embodiment of the apparatus differs from the above-described, first embodiment of the apparatus according to the invention in that the three-way valves 17, 21 and 29 are omitted. The tubings 18 and 20 are consequently connected directly to the first syringe 11, and the tubings 20 and 28 are also connected directly to a container 71. The container 71 is a flexible and collapsible bag of a plastics material such as a polyvinyl chloride bag. In the second embodiment of the apparatus or system according to the invention, the first syringe 11 comprises a string 72 which is connected to the piston rod 14 of the syringe. The piston rod 14 shown in FIG. 2 is somewhat shorter than the piston rod 14 shown in FIG. 1. —73, 74 and 75 show sites for pinching the tubings so as to block the liquid flow through the tubings. 76 shows a site for pinching the container 71.

Figure 3:
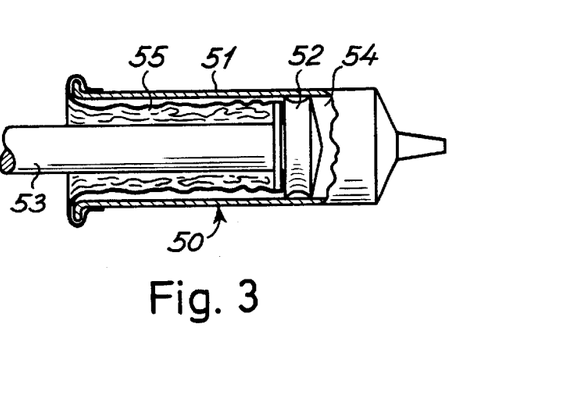
FIG. 3 is a sectional view of a modified embodiment of a container of the apparatus shown in FIG. 1 or 2.

FIG. 3 shows an embodiment of a syringe to be employed in the apparatus or system shown in FIG. 1 or FIG. 2. The syringe is designated 50 in its entirety and comprises a syringe cylinder 51, a piston 52 and a piston rod 53. The piston 52 and the syringe cylinder 51 define a chamber 54. A flexible plastic lining 55 is attached to the piston 52 and the open end of the syringe cylinder 51. During manipulation of the piston 52, the piston end of lining 55 moves with the piston 52, thus preventing contact between the collecting chamber 54 of the syringe cylinder 51 and the environment.

Figure 4:
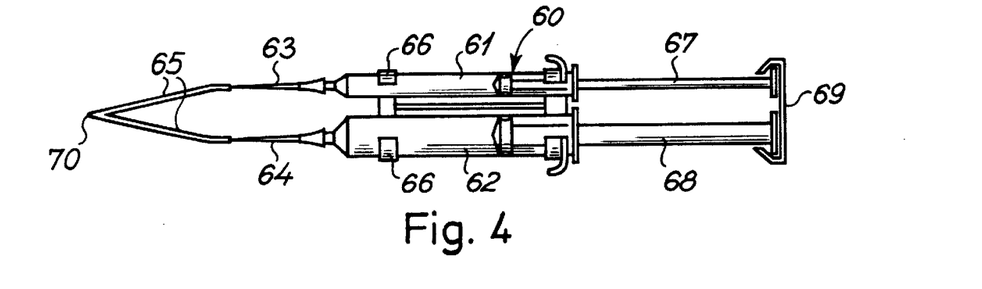
FIG. 4 is a diagrammatic side view of the two syringes used to apply the two substances used for tissue repair.

In FIG. 4 an apparatus or system, designated 60 in its entirety for application of a composition comprising tissue repair promoting substances is shown. The apparatus is used for the application of two components of a tissue-adhesive system comprising as a first component a fibrinogen-containing solution and as a second component an enzyme-containing solution.

The system comprises a first syringe 61 suitable for storing one of the substances of the two-component tissue-adhesive system and a second syringe 62 for storing the other component of the tissue-adhesive system. A needle 63 is connected to a delivery end of the first syringe 61, and a needle 64 is connected to a delivery end of the second syringe 62. A tubing 65 has its first end connected to the needle 63 and its second end connected to the needle 64. The tubing 65 is further provided with an intermediate puncture 70. The puncture 70 serves the purpose of rendering it possible to expel the two components contained in the syringes 61 and 62 at an application site of a human or animal individual. The first syringe 61 comprises a piston rod 67, and the second syringe 62 comprises the piston rod 68. The syringes 61 and 62 are supported through a supporting device 66, and the piston rods 67 and 68 are interconnected through a connection device 69 so as to render it possible to operate the piston rods 67 and 68 simultaneously.

The Application of the Tissue Repair Promoting Substances

The apparatus shown in FIG. 4 was used for the application of the two components of a tissue-adhesive system.

A syringe 61, the total volume of which was approximately 1 ml and a syringe 62, the total volume of which was approximately 3 ml, were used. The syringe 62 contained the solution comprising the tissue repair promoting substances according to the invention. The syringe 61 comprised a solution containing the enzyme thrombin (e.g. obtained from Hoffmann La-Roche) in a concentration of 1200 NIH-U/ml, and further comprising 100 mM Ca++ and 7000 KIE/ml aprotinin (Trasylol®, Bayer). The concentration of thrombin could be reduced to 5–10 NIH-U/ml when a slow conversion of fibrinogen was desired. By application of the first-mentioned solution, fibrinogen could be converted to fibrin within 5–15 sec.

The two solutions could be expelled from the system by simultaneously pressing the piston rods 67 and 68.

When the system is to be used to apply solutions at an application site in the interior of the human or animal individual, the tubing 65 may be as long as e.g. more than 1 m, the syringes (or other pressure delivery systems) being adapted thereto. Such a system may be applicable in cases in which tissue adhesion is needed e.g. subsequent to surgical biopsy in the interior of the human or animal body. In this case, the tubing 65 may be placed in a catheter and transferred within this catheter to the application site.

If the fibrinogen containing solution is gelatinating due to high concentration of fibrinogen, fluidity may be obtained within a few minutes by immersing the whole system into a sterilized water bath at approximately 37–40° C.

By means of the application apparatus, the two solutions may be kept separate until they are expelled from the system, i.e. no coagulation will take place inside the tubings or needles. (When the application system is not in use, a clot may be formed at the puncture 70 of the tubing 65, but this may easily be removed).

The invention is further illustrated by the following non-limiting examples.

EXAMPLE 1

Preparation of a Composition Containing Tissue Repair Promoting Substances From Blood From an Adult Human Donor using a Sterilized Container System Comprising Four Containers For the preparation, a system corresponding to the system shown in FIG. 1 was used. Tissue repair promoting substances present in blood plasma and cells, first of all platelets, were isolated.

Sterile chemical agents which were to be used in the preparation were filled into sterilized syringes in order to obtain a sterile system.

Syringe 11 contained 6 ml 113 mM tri-sodium citrate solution and 20 IE/ml heparin (Leo) as anticoagulants and 800 KIE/ml aprotinin as enzyme inhibitor.

Syringe 23 contained $5 \times 10^{-6}$ mol freeze-dried adenosine 5-diphosphate (ADP) to be used in promoting growth factor release from platelets.

Syringe 31 contained 2.5 ml 93 % (w/w) ethanol to be used as a chemical agent suitable for obtaining a precipitate comprising tissue repair promoting substances.

44 ml blood was collected from a human adult donor. The hematocrit value was measured to be 0.46, i.e. said blood diluted with the anticoagulant comprised 31 ml plasma fraction.

The puncture of the vein was performed by means of the needle 19, and the blood was transferred to the syringe 11 via the tubing 18. During the collection of blood and the subsequent filling of the syringe 11, the syringe was gently agitated to mix the blood with the anticoagulant.

After collection of the blood, the system was disconnected from the donor and the tubing 18 was sealed. The system was placed in an especially adapted centrifuge holder, said holder comprising compartments defining volumes suitable for the various containers of the system. Thus, the complete container system, including the tubings, could be placed in the centrifuge holder. The syringes were placed so that the delivery ends pointed upwards during centrifugation. The system was centrifuged for ten minutes at 2000×g at 15° C. in order to obtain within the syringe 11 a substantially cellfree plasma fraction, a cell-containing fraction (comprising platelets and leucocytes and a minor part of the erythrocytes), and a cell-containing plasma fraction comprising the major part of the erythrocytes.

The volume of the substantially cell-free plasma fraction was approximately 25 ml. By gently pressing the piston 13 towards the delivery end 16, 22 ml of substantially cell-free plasma fraction were transferred to the syringe 31. During this transfer the closure valves 17, 21 and 29 were positioned so as to direct the liquid flow into the syringe 31.

Subsequent to the transfer of the substantially cell-free plasma fraction, the closure valves 29 and 21 were positioned so as to direct the liquid flow into the syringe 23. The cells of the cell-containing plasma fraction comprising platelets, leucocytes and a minor part of the erythrocytes were stirred up in the remaining 3 ml plasma. By pressing the piston 13 towards the delivery end 16, said cell-containing plasma fraction was transferred to the ADP-containing syringe 23. The syringe 11 was disconnected and the biological material was either discarded or used for alternative purposes such as transfusion of the erythrocyte fraction to the human donor from whom the blood had initially been taken.

The syringes 23 and 31 were treated so as to obtain thorough mixing of the materials contained therein. During this period, the ADP promoted the release of tissue repair promoting substances such as PDGF. The whole system was subsequently incubated in an ice bath at 0° C. for approximately 30 minutes. During this period the ethanol precipitation took place in the syringe 31. If optionally the syringe 23 is incubated in e.g. an ice bath, the low temperature causes a partial disrupture of cellular structures of the cells, first of all the platelets, present in the syringe 23, thereby releasing tissue repair promoting substances from the cells, including e.g. the platelet-derived growth factor and the epidermal growth factor.

After the incubation period, the container system was centrifuged for 10 minutes at 2000×g at approximately 0° C. Thus, the precipitate obtained in the syringe 31 was comprised in a firm pellet separated from the remaining part of the plasma fraction. At the same time, the cells and cell residues within the syringe 23 were sedimented, and thus a fraction enriched with tissue repair promoting substances from the cells, primarily platelets, (a "cell extract") was obtained.

The syringe 31 was turned upside down, i.e. the delivery end 30 pointed downwards. The closure valve 29 was positioned so as to direct the liquid flow from the syringe 31 to the tubing 36 of the container 37. By pressing the piston 33 towards the delivery end 30, the non-precipitated plasma material was transferred to the container 37 via the tubing 36. During this procedure, the air present in the syringe 31 facilitated the separation of the plasma fraction from the sedimented precipitate.

The closure valves 21 and 29 were positioned so as to direct the liquid flow from the syringe 23 to the syringe 31. By pressing the piston 25 towards the delivery end 22 of the syringe 23, a part of the cell extract, typically approximately 0.2 ml, sufficient for obtaining a dissolved precipitate, was transferred to the tubing 28 and subsequently into the collecting chamber 35 of the syringe 31. Thus, the tissue repair promoting substances to be used were contained in the chamber 35 of the syringe 31. The syringe 31 was incubated at 37° C. in order to dissolve the precipitate in the cell extract. If needed, further amounts of cell extract could be added in order to facilitate dissolution of the precipitate.

After approximately 10 minutes the precipitate was dissolved, and approximately 1.5 ml of the solution comprising the tissue repair promoting substances was obtained. This solution could be used immediately or alternatively stored until use, e.g. stored in a frozen state.

The resulting solution contained 26 g/l of fibrinogen, and the recovery of fibrinogen was 84% of the amount present in the 22 ml plasma fraction (containing 2.1 g/l), or 60% of the amount present in the 44 ml of blood collected. The method used for determination of fibrinogen was based on the conversion of fibrinogen into fibrin which was subsequently isolated and assayed. (cf. O. D. Ratnoff et al., J. Lab. Clin. Med. 37, 1951, p 316; W. D. Sawyer et al., Thromb. Diath. Haem. 5, 1961, p 149; and T. Astrup et al., Scand. J. Clin. & Lab. Invest. 17, 1965, 57). The assay is a "functional assay" in that only the fibrinogen which is convertible to fibrin is determined. Thus, the values representing the fibrinogen recoveries indicate the recovery of biologically active fibrinogen, i.e. fibrinogen useful in obtaining tissue adhesion.

The platelets comprised in the 3 ml plasma were concentrated from the 44 ml of whole blood. 0.2 ml of the cellular extract contained growth factors corresponding to maximally 2.9 ml of whole blood.

EXAMPLE 2

Preparation of Composition Containing Tissue Repair Promoting Substances From Blood From an Adult Human Donor using a Sterilized Container System Comprising Three Containers For the preparation a sterilized container system corresponding to the system shown in FIG. 2 was used. Tissue repair promoting substances present in blood plasma and cells (first of all platelets) were isolated.

The syringe 11 contained various chemical agents (cf. Example 1), the collapsible bag 71 was empty, and the syringe 31 contained ethanol (cf. Example 1).

Blood was collected from a human adult donor in a way similar to the way described in Example 1.

After collection of the blood, the system was disconnected from the donor and the tubing 18 was sealed by pinching the tubing 18 with an aluminium clip at the site 73. The container system was placed in a centrifuge holder without any of the containers being disconnected from each other. The system was centrifuged for 15 minutes at 250×g at 15° C. in order to obtain a platelet-enriched plasma fraction. Thus, the major part of the supernatant was constituted by this fraction, and the major part of the pellet was constituted by the erythrocytes.

By gently pressing the piston rod 14 towards the delivery end 16, the major part of the platelet-enriched plasma fraction was transferred to the container bag 71. During this transfer, the passage through the tubing 28 was blocked by an aluminium clip pinching the tubing 28 at the site 75.

Subsequent to the transfer of the platelet-enriched plasma fraction, an aluminium clip was used for pinching the tubing 20 at the site 74. The syringe 11 was disconnected and the biological material was either discarded or used for alternative purposes such as transfusion of the erythrocyte fraction to the human donor who had contributed the blood.

The container system was centrifuged for 10 minutes at 2000×g at 15° C. in order to sediment cells, first of all platelets, within the second container 71.

The volume of the container bag 71 was temporarily divided into a first chamber containing the sedimented platelets and a minor part of the plasma and a second chamber containing the major part of the plasma. This division was obtained by pinching the walls of the container 71. Subsequently, the aluminium clip at the site 75 of the tubing 28 was removed while the ethanol content of the syringe 31 was transferred to the second chamber of the container bag 71 by pressing the piston rod 34 towards the delivery end 30 of the syringe 31. After the transfer, the aluminium clip was replaced at the site 75 of the tubing 28, and the syringe 31 could subsequently be disconnected. The platelets were resuspended in the plasma present in the first chamber of the container bag 71 by shaking the container 71.

The whole system was incubated at −20° C. so as to precipitate the tissue repair promoting substances in the second chamber, and so as to disrupt the cellular structures of the cells contained in the first chamber thereby releasing tissue repair promoting substances from the platelets, thus obtaining a fraction enriched with tissue repair promoting substances released from the platelets. Subsequently, the system was subjected to approximately 2° C. for approximately 20 minutes and centrifuged at 2000×g at approximately 0° C. for 15 minutes in order to sediment the precipitate within the second chamber and the cells and cellular residues within the first chamber.

The chambers were further subdivided by pinching, e.g. by means of aluminium clips, the flexible walls of the container 71, first by pinching just above the precipitate and then pinching the wall parts just above the pellet constituted by the cells and cellular residues adhering to the bottom part of the bag 71. The primary temporary division of the second container was abolished, obtaining a combined chamber comprising the third fraction enriched with tissue repair promoting substances released from the platelets and the second fraction comprising the major part of the precipitate. Thus, all the desired tissue repair promoting substances were now contained in the combined chamber formed between the two pinching sites. The container 71 comprising the combined chamber was incubated at 37° C. in order to dissolve the precipitate in the platelet extract. (Alternatively, the container 71 could be stored until use prior to this incubation step.) For further details concerning dissolving time and storage time, vide Example 1.

EXAMPLE 3
Preparation of a Composition Containing Tissue Repair Promoting Substances From Blood From an Adult Human Donor using a Sterilized Container System Comprising Four Containers For the preparation a sterilized system corresponding to the system shown in FIG. 1 is used, with the exception that all four containers are collapsible flexible plastic bags comprising volumes adapted to the fractions obtained, said bags being interconnected by tubings comprising valves. Tissue repair promoting substances naturally present in plasma and in platelets are isolated.

Chemical agents which are to be used in the preparation are filled into the containers, and the whole system comprising the agents is sterilized prior to use.

The syringe 11 contains agents as described in Example 1.
The syringe 23 and 37 are empty.
The syringe 31 contains ethanol as described in Example 1.

Human blood is collected from a voluntary donor as described in Example 1.

The system is centrifuged so as to obtain a fraction essentially comprising erythrocytes, a fraction essentially comprising the leucocytes, and a fraction comprising a platelet-enriched plasma fraction.

The platelet-enriched plasma fraction is transferred to the container 37.

The fraction essentially comprising leucocytes is transferred to the syringe 23.

The syringe 11 essentially comprising the erythrocytes and the syringe 23 essentially comprising the leucocytes are disconnected and the biological materials may be used for alternative purposes.

The system comprising the syringe 31 and the container 37 is centrifuged so as to sediment the platelets in the container 37. The volume of the container 37 is divided so as to obtain a first chamber comprising the platelets and a minor part of the plasma and a second chamber comprising the major part of the plasma. The ethanol comprised in a syringe 31 is transferred to the second chamber of the container 37. The composition comprising tissue repair promoting substances derived from plasma and platelets is isolated within the container 37 as described in Example 2.

As a further modification of the method described in this Example, the container system may comprise a fifth container containing SAG-M solution (e.g. per 100 ml: sodium chloride 877 mg, anhydrous dextrose 818 mg, mannitol 525 mg, adenin 16.9 mg). The SAG-M solution may be transferred to the residual erythrocyte fraction (i.e. the erythrocyte fraction obtained in the syringe 11 after the removal of the platelet-enriched fraction and the leucocyte and platelet comprising fraction). The addition of the SAG-M solution to the erythrocyte fraction is useful when this fraction is to be preserved for transfusion.

EXAMPLE 4
Preparation of a Composition Containing Tissue Repair Promoting Substances From Blood From a Human Donor using a Sterilized Container System Comprising Two Containers For the preparation a sterilized system corresponding to the system shown in FIG. 2 was used, with the exception that the syringe 31 is omitted. The syringe 11 is a syringe and the container 71 is a flexible plastic bag. Tissue repair promoting substances naturally present in plasma are isolated.

The syringe 11 contains agents as described in Example 1.
The container 71 contains 2.5 ml 93% (w/w) ethanol.
The human blood is collected as described in Example 1.
The system is centrifuged in order to obtain a first fraction essentially comprising plasma and a second fraction essentially comprising the blood cells.

The plasma fraction is transferred to the container 71, the transfer being similar to the transfer described in Example 2. The tubing 20 is sealed by pinching with an aluminium clip at the site 74. The syringe 11 may then be disconnected, and the material used for alternative purposes.

The container 71 is incubated in an ice bath at 0° C. for approximately 30 minutes. During this period, the ethanol precipitation takes place in the container 71.

After the incubation period, the container system is centrifuged for 10 minutes at 2000×g at 0° C.

The volume of the container 71 is divided into a first and second chamber by pinching the flexible walls of the container 71. The first chamber comprises the precipitate and a minor part of the plasma. The container 71 is incubated at 37° C. in order to dissolve the precipitate in the plasma fraction. If needed, an appropriate amount of sterile liquid such as saline may be injected into the container 71 in order to facilitate the dissolving of the precipitate. If appropriate, the container 71 can be stored until use prior to the incubation step.

EXAMPLE 5
Preparation of Compositions Comprising Tissue Repair Promoting Substances Prepared as Described In Example 4, but With Variations In the Ethanol Concentration, Incubation Temperature and pH In order to study the effect of the ethanol concentration, the incubation temperature, and the pH during the precipitation, various preparations were obtained in a similar manner as described in Example 4. Plasma fractions were obtained after centrifugation for 10 minutes at 2000×g at 15° C. The plasma fractions were incubated with varying amounts of 93% w/w ethanol giving concentrations from 6.2% to 9.4% at 0° C. or −3° C., at pH 7.8 or 6.2. pH 6.2 was obtained by the addition of 113 mmolar citric acid to the plasma before the ethanol precipitation. The precipitates were centrifuged for 10 minutes at the incubation temperature of 2000×g.

Subsequent to the isolation of the fraction comprising the precipitate (comprising the tissue repair promoting substances), said precipitate was incubated at 37° C. for 20 minutes. In four of the experiments, the precipitate was not completely dissolved and plasma was added to give a homogeneous solution.

The concentration of fibrinogen was measured as described in Example 1. Results are shown in Table I.

The concentration of the factor XIII was measured by rocket immunoelectrophoresis according to Laurell's method. Anti-human factor XIII-A rabbit serum was obtained from Diagnostica Stago. A plasma sample was used as standard. The concentration of factor XIII in the solution prepared was usually in the order of approximately 20–25 times the concentration of factor XIII in the plasma of the blood samples collected.

TABLE I

| Ethanol concentration w/w % | Incubation temp. °C. | pH during precipitation | Addition of plasma in % of the initial volume | Fibrinogen in the fraction obtained g/l | % Recovery of the plasma fibrinogen |
|---|---|---|---|---|---|
| 6.2 | 0 | 7.8 | 0 | 41 | 82 |
| 9.4 | 0 | 7.8 | 1 | 36 | 67 |
| 6.2 | −3 | 7.8 | 0 | 35 | 70 |
| 9.4 | −3 | 7.8 | 1 | 31 | 74 |
| 6.2 | 0 | 6.2 | 2 | 39 | 75 |
| 9.4 | 0 | 6.2 | 2.4 | 33 | 89 |

The fibrinogen concentration in plasma, corrected for the dilution with the anticoagulant, was 2.6 g/l.

EXAMPLE 6
Preparations as Described In Example 5 with Further Modifications of the Ethanol Concentration and the Incubation Time In these experiments the tissue repair promoting substances were precipitated with 93% ethanol to give concentrations varying from 7.8% to 10.9% w/w. After incubation at 0° C. for different time intervals, the precipitates were separated and varying amounts of plasma were added to the precipitates before the incubation at 37° C. After 10 to 15 minutes homogeneous solutions were obtained. The concentration of fibrinogen was determined as described in Example 1. The concentration in plasma was corrected so as to compensate for the dilution caused by the addition of the chemical agents including the anticoagulants. The results are shown in Table II.

TABLE II

| Donor | Ethanol w/w % | Time of Incubation, min. | Addition of plasma in % of initial volume | Fibrinogen concentration g/l in Plasma | Fraction obtained | % Recovery of the plasma fibrinogen |
|---|---|---|---|---|---|---|
| A | 7.8 | 50 | 5 | 2.4 | 18 | 82 |
|   | 9.4 | — | 5 | — | 16 | 82 |
|   | 10.9 | — | 5 | — | 18 | 91 |
| B | 7.8 | 45 | 2.5 | 2.3 | 19 | 72 |
|   | 9.4 | — | 2.5 | — | 20 | 79 |
|   | 10.9 | — | 2.5 | — | 20 | 89 |
| C | 7.8 | 120 | 2.5 | 2.6 | 30 | 83 |
|   | 9.4 | — | 2.5 | — | 32 | 89 |
|   | 10.9 | — | 2.5 | — | 28 | 95 |

EXAMPLE 7
Preparation of a Composition Containing Tissue Repair Promoting Substances from Blood from a Human donor using a Sterilized Container System Comprising Two Containers For the preparation, a sterilized system corresponding to the system shown in FIG. 2 was used, with the exception that the syringe 31 was omitted. Tissue repair promoting substances naturally present in plasma and platelets were isolated.

The syringe 11 contained agents as described in Example 1.

The collapsible bag 71 was empty.

The human blood was collected as described in Example 1. The system was centrifuged for 15 minutes at 250×g at 15° C. in order to obtain a platelet-enriched plasma fraction.

The platelet-enriched plasma fraction was transferred to the container 71. The syringe 11 essentially comprising erythrocytes and leucocytes was disconnected from the container 71.

The container 71 was centrifuged so as to sediment the platelets. The volume of the container 71 was divided so as to obtain a first chamber comprising the platelets and a minor part of the plasma and a second chamber comprising the major part of the plasma.

The container 71 was incubated at −20° C. and the tissue repair promoting substances derived from plasma and platelets were isolated within the container 71 as described in Example 2.

The resulting solution (1.5 ml) contained 15 g/l of fibrinogen, and the recovery of fibrinogen was 34% of the amount present in the plasma fraction (25 ml containing 2.6 g/l of fibrinogen).

EXAMPLE 8
Preparation of a Composition Containing Tissue Repair Promoting Substances Naturally Present in Plasma Isolated from Human Donor Blood The composition was prepared using a sterilized system corresponding to the one used in Example 4.

The syringe 11 (cf. FIG. 2) contained 6 ml 113 mM tri-sodium citrate solution and 20 lE/ml heparin.

The container 71 contained 6 ml 42% (w/w $(NH_4)_2SO_4$) solution.

Human blood was collected as described in Example 1. The system was centrifuged, and the fraction comprising the major part of the plasma was transferred to the container as described in Example 4.

After mixing the plasma fraction with the $(NH_4)_2SO_4$ solution, the container 71 was centrifuged for ten minutes at 2000×g at 4° C.

The precipitate was separated and dissolved as described in Example 4. 70% of the fibrinogen present in the plasma was precipitated by this procedure.

EXAMPLE 9
Preparation of a Composition Containing Tissue Repair Promoting Substances Isolated from the Blood of an Adult Female Rabbit and in vivo Testing The composition was prepared using a sterilized system corresponding to the one shown in FIG. 1. Tissue repair promoting substances present in blood plasma and cells (primarily platelets) were isolated.

The syringe 11 contained 4 ml 113 mM tri-sodium citrate solution and 20 IE/ml heparin as anticoagulants and 800 KIE/ml aprotinin as a proteolytic enzyme inhibitor.

The syringe 23 contained adrenalin 0.05 ml 0.1% solution to be used for promoting growth factor release from platelets.

The syringe 31 contained 2 ml 93% (w/w) ethanol.

26 ml blood was collected from a nembutal anesthetized female rabbit weighing 4 kg by means of the needle 19 inserted in a jugular vein.

After collection of the blood, the system was disconnected from the rabbit and the tubing 18 was sealed. The system was centrifuged as described in Example 1.

The volume of the substantially cell-free plasma fraction was approximately 22 ml. 20 ml were transferred to the syringe 31 and 2 ml were used to stir the platelets, leucocytes and a minor fraction of erythrocytes. This cell-containing plasma fraction was transferred to the syringe 23 as described in Example 1. The syringe 11 containing the erythrocytes was disconnected, and the erythrocytes were resuspended in 50 ml sterile saline. This suspension was retransfused to the rabbit.

The composition comprising tissue repair promoting substances derived from plasma and platelets were isolated as described in Example 1.

The volume of the resulting solution was 1.15 ml, and it contained 29 g/l of fibrinogen. 87% of the plasma fibrinogen was recovered.

The fibrinogen-containing solution was applied simultaneously with a sterile solution containing 1200 NIH/ml thrombin, 100 mM $CaCl_2$ and 7000 KIE/ml aprotinin, during a microsurgical tubal anastomosis procedure performed on the rabbit from which the blood had been collected within one hour after collection.

For the application of the two components, the apparatus shown in FIG. 4 was used. The apparatus was sterilized prior to use, and kept sterile—externally and internally—during the entire procedure. The fibronogen-containing solution was transferred to the 3 ml syringe 62 and the thrombin-containing solution was transferred to the 1 ml syringe 61. The two syringes were placed in the supporting device 66. The needles 63 and 64 were connected with the tubing 65 and mounted on the syringes. During application, the two pistons 67 and 68 were pressed simultaneously by means of the connective device 69. The fibrinogen-containing solution and the thrombin solution were mixed in the proportion 1 to 0.3 at the puncture 70 of the tubing 65. Approximately 10 to 15 seconds after mixing, fibrinogen was converted to fibrin and a stable clot was formed within 3 minutes.

The rabbit was subjected to bilateral microsurgical transection of the istmus, 1 to 3 cm from the corner of the uterus. A 1 cm portion of the tube was excised, followed by end-to-end tubal anastomosis. The proximal and distal segments of the oviduct were assembled by a clamp while the fibrinogen adhesive was applied. Three minutes later the clamp was removed. No ordinary suture was used for the anastomosis.

Four weeks after the operation, the rabbit was mated. Immediately before delivery it was killed. By dissection, fetuses were observed in both uterine horns. No adhesion formation was observed.

EXAMPLE 10
Preparation of a Composition Containing Tissue Repair Promoting Substances Isolated from the Blood of a Pig The composition was prepared in a sterilized system corresponding to the one shown in FIG. 1. Tissue repair promoting substances present in blood plasma were isolated.

The syringe 11 contained 6 ml 113 mM tri-sodium citrate solution and 20 IE/ml heparin as anticoagulants, and 8 mM ∊-aminocaproic acid as a fibrinolytic inhibitor.

The syringe 23 was empty.

The syringe 31 contained 3 ml ethanol 92% (w/w). 44 ml blood were collected from a nembutal anesthetized pig weighing 32 kg by means of the tubing 18 directly inserted in a jugular vein. After collection of the blood, the system was disconnected from the pig and the tubing 18 was sealed. The system was centrifuged as described in Example 1.

The volume of the substantially cell-free plasma was approximately 33 ml. 31 ml were transferred to syringe 31 and 2 ml were transferred to syringe 23. The syringe 11 essentially comprising the erythrocytes was disconnected and discarded.

The tissue repair promoting substances present in plasma were isolated as described in Example 1. The fibrinogen-containing precipitate was dissolved in 0.3 ml ethanol-free plasma transferred from syringe 23.

The volume of resulting solution was 2.9 ml, and it contained 27 g/l of fibrinogen. 89% of the plasma fibrinogen was recovered.

The solution was stored at −20° C. for three days.

The frozen solution was transferred to 37° C. and liquefaction was attained within 15 minutes on the day of surgery (performed on the pig from which the blood had been collected).

The application was performed as described in Example 9.

In the nembutal anesthetized pig, the liver was exposed by laparatomy. In a lobe an incision of approximately 6 cm in length was cut from the margo towards the central part of the lobe. To reduce bleeding, hemostasis was partly obtained by means of an intestinal clamp. The wound cleft was assembled simultaneously with the application of the fibrinogen adhesive, and a manual mild pressure was applied for approximately 3 minutes. After release of the pressure and the intestinal clamp, minor bleeding spots were sealed with the adhesive.

No postoperative complications were observed. One month after the incision there were no macroscopic signs of damage. Histological preparations showed a minor scar of connective tissue—invaginated with blood vessels—approximately three times the size of normal connective tissue present in pig liver.

What is claimed is:

1. A tissue repair promoting composition comprising tissue repair promoting substances isolated from plasma and tissue repair promoting substances isolated from platelets, the tissue repair promoting substances isolated from plasma including at least fibrinogen, the composition being substantially free of fibrin.

2. The composition of claim 1 wherein the tissue repair promoting substances isolated from plasma further include factor XIII and fibronectin.

3. The composition of claim 1 wherein the tissue repair promoting substances isolated from platelets include at least one growth factor.

4. The composition of claim 3 wherein the tissue repair promoting substances isolated from platelets include platelet-derived growth factor, epidermal growth factor or both.

5. The composition of claim 1 wherein the tissue repair promoting substances isolated from platelets include platelet factors 1–4.

6. The composition of claim 1 wherein the tissue repair promoting substances isolated from platelets include platelet factor 2.

7. The composition of claim 2 wherein the tissue repair promoting substances isolated from platelets include at least one growth factor.

8. The composition of claim 7 wherein the tissue repair promoting substances isolated from platelets include platelet-derived growth factor, epidermal growth factor or both.

9. The composition of claim 2 wherein the tissue repair promoting substances isolated from platelets include platelet factors 1–4.

10. The composition of claim 2 wherein the tissue repair promoting substances isolated from platelets include platelet factor 2.

11. The composition of any one of claims 1–10 which is in liquid form.

12. The composition of claim 1 wherein the tissue repair promoting substances are isolated from the plasma and platelets of a single human or animal.

* * * * *